United States Patent [19]

Ritland

[11] Patent Number: 5,242,140
[45] Date of Patent: Sep. 7, 1993

[54] CASTING STAND

[76] Inventor: Gerald D. Ritland, 79 Timberwood Rd., West Hartford, Conn. 06117

[21] Appl. No.: 906,821

[22] Filed: Jun. 30, 1992

[51] Int. Cl.5 .............................................. F16L 3/00
[52] U.S. Cl. ...................................... 248/122; 602/39
[58] Field of Search ...................... 248/122; 49/46, 47; 269/901, 71, 17; 602/39; 5/630, 83.1, 648

[56] References Cited

U.S. PATENT DOCUMENTS

| | | | |
|---|---|---|---|
| 725,850 | 4/1903 | Konigstein | 248/122 |
| 1,045,583 | 11/1912 | Mills | 248/122 X |
| 2,019,326 | 10/1935 | Stuart | 49/47 |
| 2,498,115 | 2/1950 | Purgett | 602/39 |
| 2,654,147 | 10/1953 | Wilson et al. | 248/122 X |
| 3,139,884 | 7/1964 | Stryker . | |
| 3,554,191 | 1/1971 | Barnes . | |
| 3,908,643 | 9/1975 | Bliss . | |
| 3,913,717 | 10/1975 | Collins | 49/46 X |
| 3,914,902 | 10/1975 | Lamberson | 49/47 |
| 4,261,348 | 4/1981 | Hargadon . | |
| 4,706,915 | 11/1987 | Cindric et al. | 248/122 |
| 4,726,363 | 2/1988 | Hergenroeder . | |
| 4,941,463 | 7/1990 | Hergenroeder . | |
| 5,072,543 | 12/1991 | Tetherton | 49/47 |
| 5,121,898 | 6/1992 | Komada | 248/122 |

Primary Examiner—Blair M. Johnson
Attorney, Agent, or Firm—Chilton, Alix & Van Kirk

[57] ABSTRACT

A casting stand for applying a cast to a foot and/or lower leg, comprising a base, an upright telescoping support post mounted on the base and a limb support turnstile rotatably mounted on the upper end of the post. The turnstile has two different elongated foot support blades and is rotatable to individually place each of the support blades in a working position to support a foot for application of a cast.

17 Claims, 3 Drawing Sheets

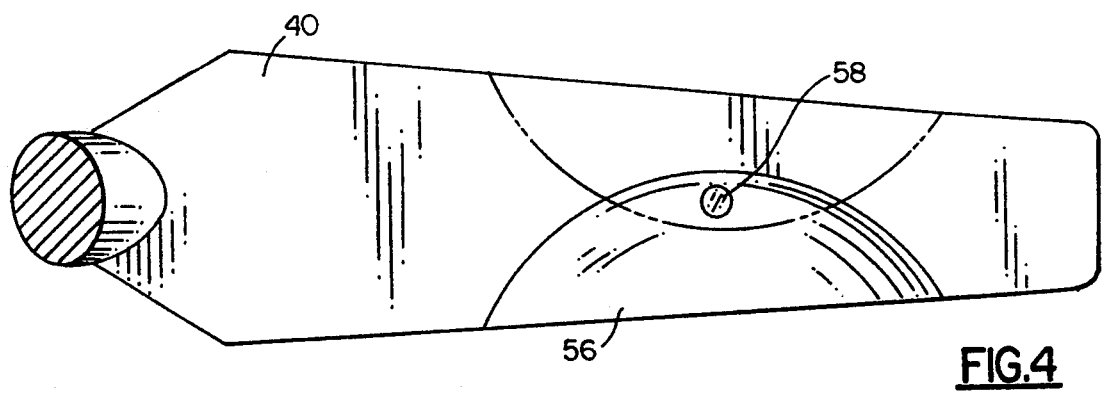
FIG.4
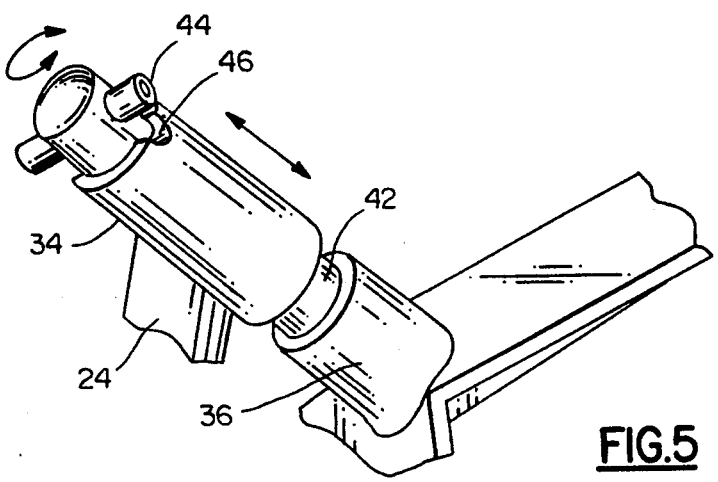
FIG.5
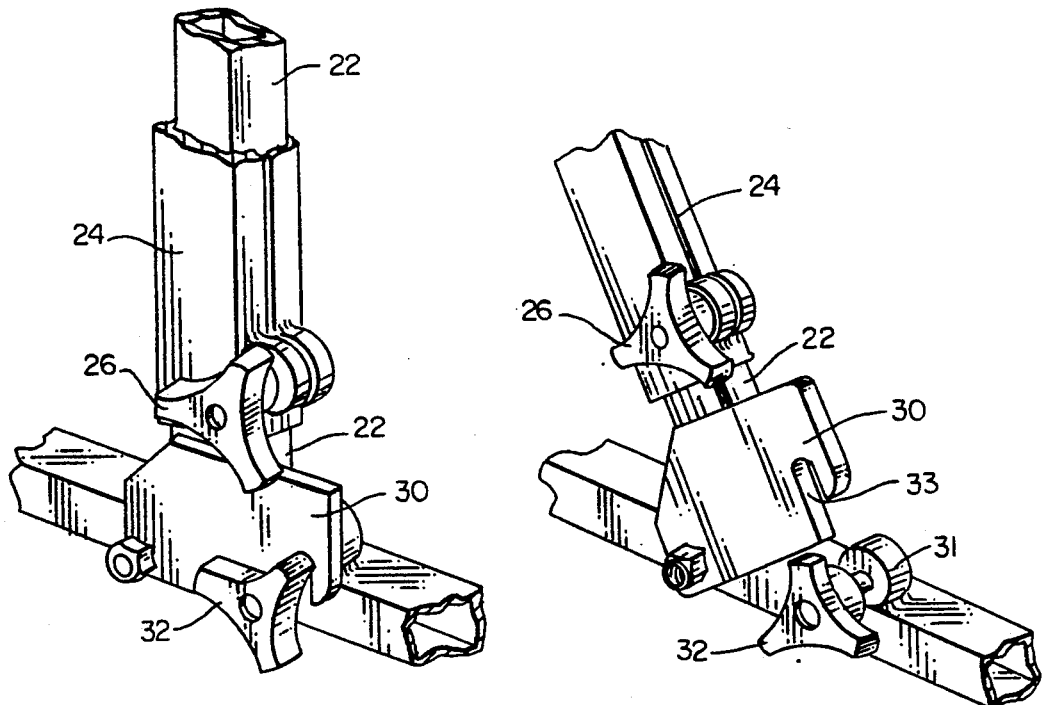
FIG.6
FIG.7

CASTING STAND

BACKGROUND AND SUMMARY OF THE INVENTION

The present invention generally relates to casting stands of the type used for supporting a foot and leg while applying a cast and more particularly relates to a new and improved casting stand having multiple limb supports which can be independently used during the application of a cast without the need for an assistant.

A principal object of the invention is to provide a new and improved casting stand for supporting a patient's foot in a desired position during each step of a two-step process of applying a cast to the foot and/or lower leg.

Another object of the invention is to provide a new and improved casting stand which facilitates applying a cast to a patient's foot so that the cast is more comfortable to the patient.

Yet another object of the invention is to provide a new and improved casting stand that is specifically adapted for applying a walking cast to a patient's foot and/or lower leg.

Another object of the invention is to provide a new and improved casting stand which enables a cast to be applied by a physician or technician without assistance.

Yet another object of the invention is to provide a new and improved casting stand having a plurality of differently configured and selectively useable limb supports.

A further object of the invention is to provide a new and improved casting stand of the type described that can be easily folded for storage and transport and unfolded and erected for use.

Another object of the invention is to provide a new and improved casting stand of the type described having a component for molding the arch of the foot into the cast, which is selectively useable for a right foot and left foot.

Yet another object of the invention is to provide a new and improved casting stand which is durably constructed and adapted to be economically manufactured.

Other objects will be in part obvious and in part pointed out more in detail hereinafter.

BRIEF DESCRIPTION OF THE DRAWINGS

In the drawings:

FIG. 4 is an enlarged, partial plan section view, partly in section, of the stand showing a secondary support blade in a working position thereof and showing an arch support form in alternative positions thereof in solid and broken lines;

FIG. 5 is an enlarged, partial perspective view, partly broken away, of the stand showing a shaft detent mechanism;

FIGS. 6 and 7 are enlarged, partial perspective views, partly broken away, of the stand showing a telescoping post and post mounting mechanism;

DESCRIPTION OF THE PREFERRED EMBODIMENT

Figure 1:
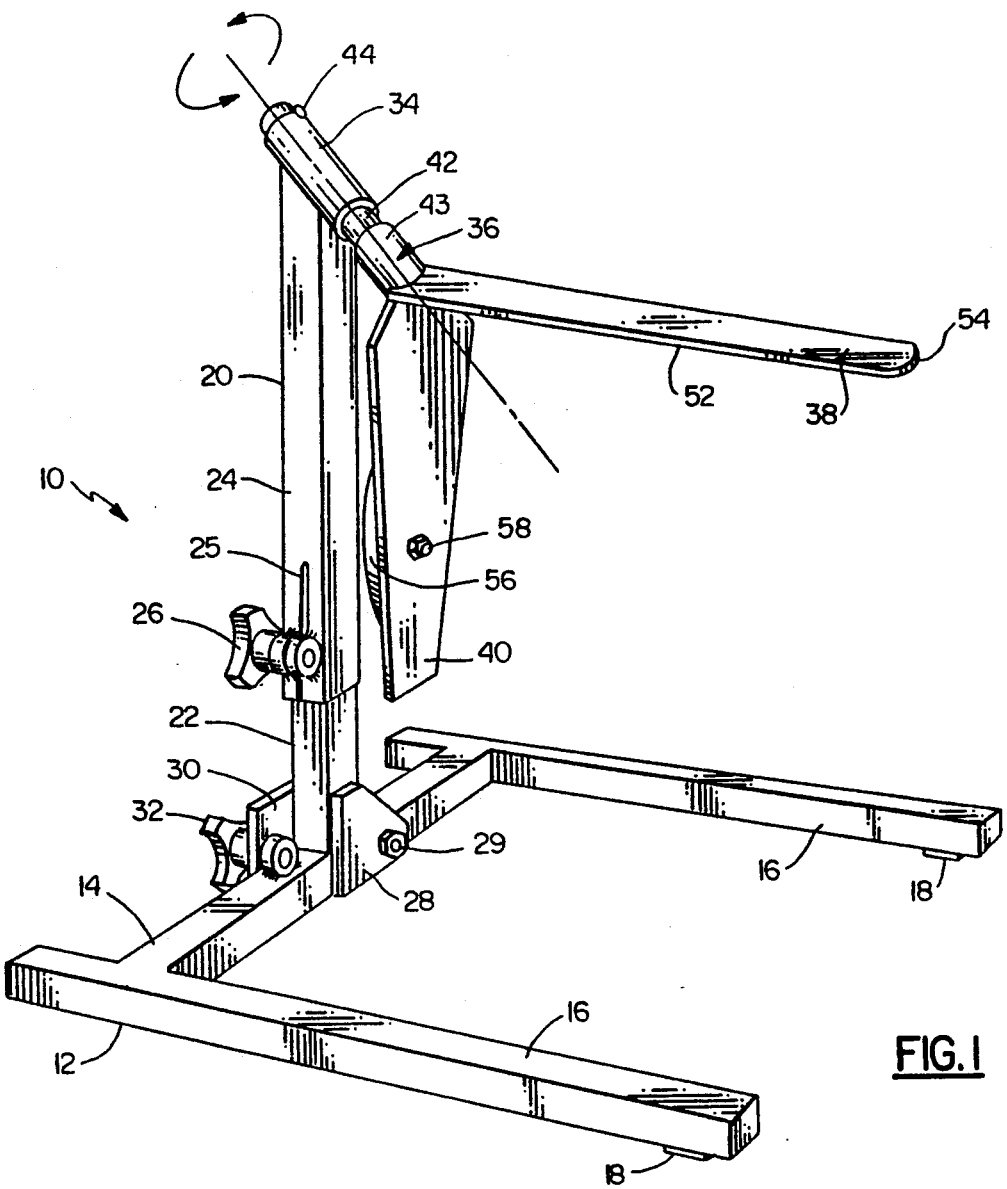
FIG. 1 is a perspective view of a new and improved casting stand according to the present invention, showing a primary support blade in a horizontal working position.
Figure 2:
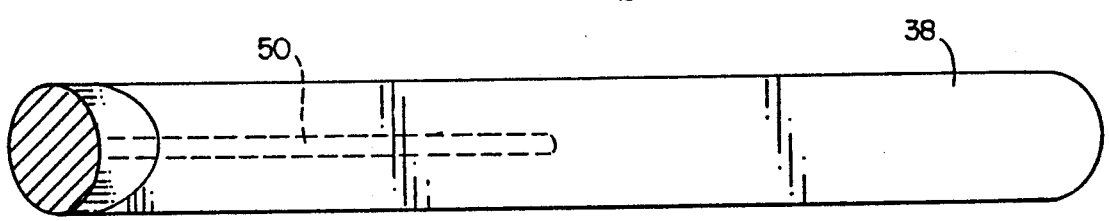
FIG. 2 is an enlarged, partial plan section view, partly in section, of the stand showing the primary support blade in greater detail.

In the drawings, like numerals are used to identify the same or like parts. Referring particularly to FIG. 1, a casting stand 10 according to the present invention is shown unfolded and erected ready for use. The casting stand 10 has a flat, H-shaped supporting base 12 with a crossbar 14 extending between a pair of parallel legs 16. A non-skid pad 18 is provided on the bottom of each leg 16. A central support post 20 is mounted on the crossbar 14. The support post 20 has lower and upper telescoping sections 22, 24. The upper, outer section 24 is adjustable on the lower, inner section 22 for adjusting the height of the stand 10. The upper section 24, at its lower end, has a vertical slot 25 and a knob operated clamping screw 26 for locking or clamping the upper section 24 onto the lower section 22. The lower section 22 tapers slightly inwardly in a direction away from the base 12 to prevent the upper section 24 from slipping downward over the lower section 22 when the clamp 26 is tight. The lower section 22 is pivotally mounted on the base 12 by a pair of opposed flanges 28, 30 which are fixed to the lower section 22 and pivotally connected by a pivot pin or stud 29 to the crossbar 14. The lower end face of the lower section 22 rests on the crossbar 14 to support the post 20 in a vertical or upright position.

A second knob operated clamping screw 32 is mounted on the crossbar 14 for locking the support post 20 in its vertical position. The outer flange 30 has an elongated slot 33 for receiving the shaft of the clamping screw 32 when the support post 20 is upright. The clamping screw 32 serves to clamp the flange 30 between the head of the screw 32 and a screw mounting lug 31 welded to the crossbar 14.

A bearing sleeve or trunnion 34 is welded to the top of the post 20. The axis of the sleeve 34 extends downwardly and forwardly at an angle of 45° to the axis of the post 20 within a vertical plane which is parallel to and bisects the legs 16 of the base 12.

A turnstile-like rotor 36 has an integral shaft 42 received within the bearing sleeve 34. In the shown embodiment, the turnstile 36 has two elongated limb support blades 38, 40, each extending outwardly from the axis of the turnstile 36 at an angle of 45° and which in combination with the shaft 42 have a generally Y-shaped configuration. The axes of the shaft 42 and two blades 38, 40 lie in the same plane and the two blades 38, 40 extend at right angles to each other and are angularly spaced 180° about the axis of the shaft 42. The blades 38, 40 are welded to a sleeve 43 which is affixed to the lower front end of the shaft 42. The shaft 42 and sleeve therefore provide a mounting hub for the blades 38, 40. The turnstile 36 is manually rotatable to rotate each blade 38, 40 to an upper horizontal working position to support a patient's foot. The other blade is then retained in a storage position parallel to and adjacent the vertical post 20. A diametral detent pin 44 mounted on the rear end of the shaft 30 is received within diametrally opposed detent slots 46 in the rear end face of the bearing sleeve 34 to hold the turnstile 36 in each of its two working positions.

Figure 3:
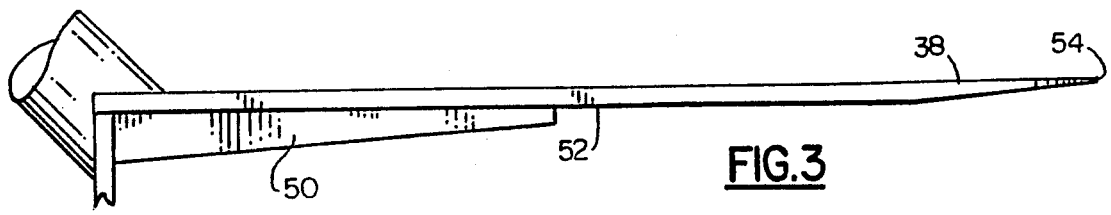
FIG. 3 is an enlarged, partial side elevation view, partly broken away, of the stand showing additional details of the primary support blade.
Figure 8:
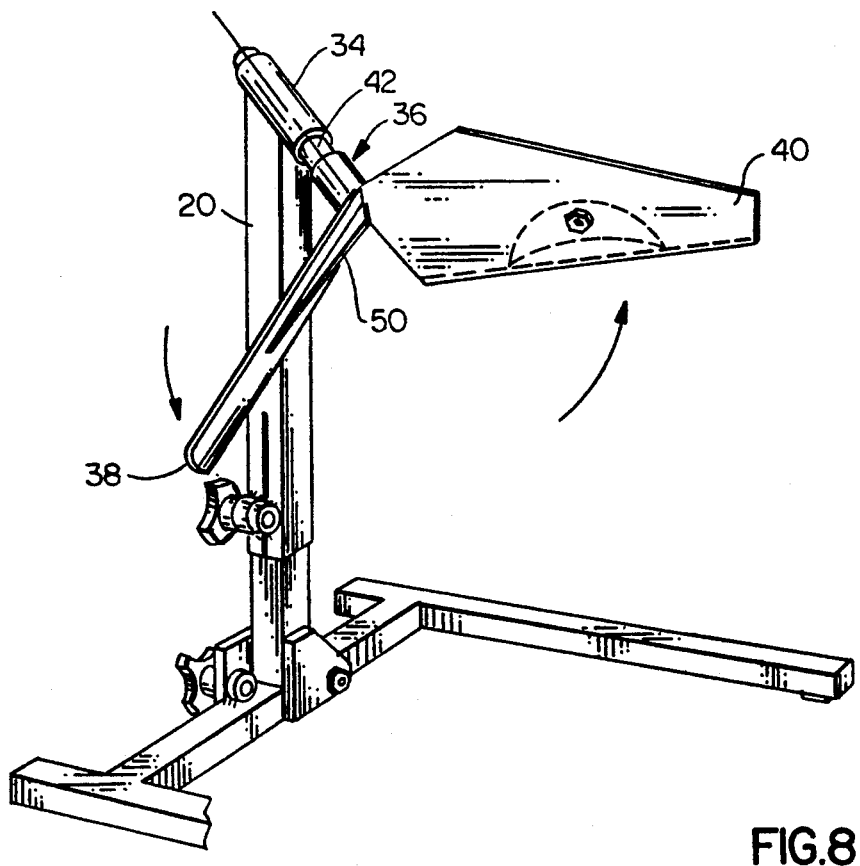
FIG. 8 is a partial perspective view, partly broken away, of the stand illustrating rotation of a support blade turnstile to rotate the secondary support blade to its working position.
Figure 9:
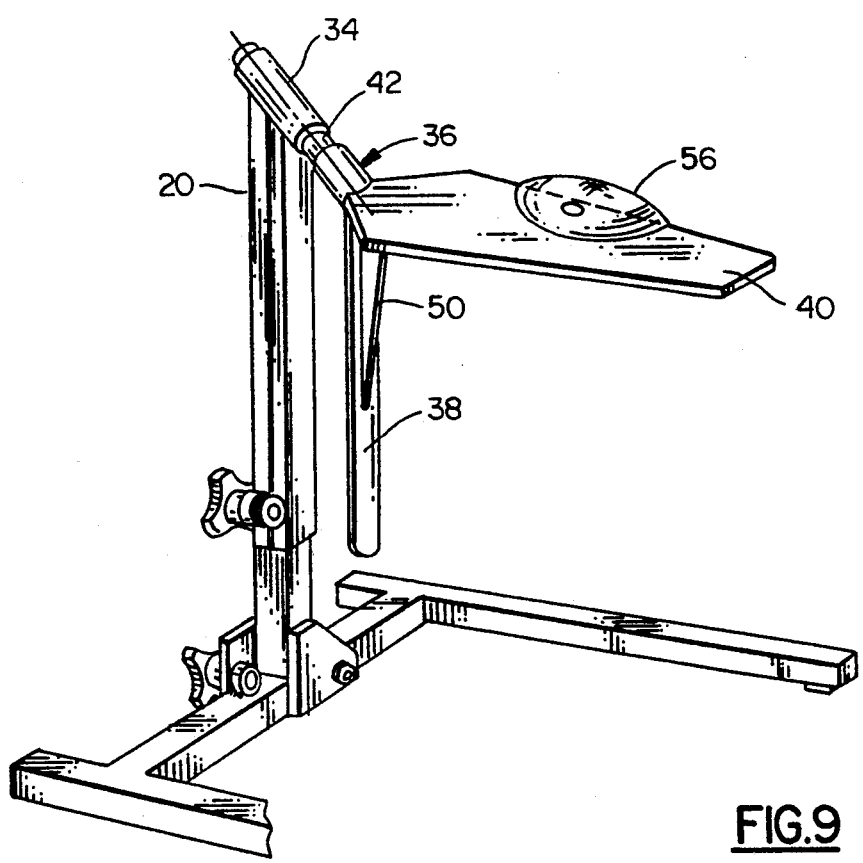
FIG. 9 is partial perspective view, partly broken away, of the stand showing the secondary support blade in its working position.

In the embodiment shown, the blades 38, 40 are provided by flat elongated plates. The primary blade 38 is about 10 inches long, 1¼ inches wide, and has an outer rounded end 54. The secondary blade 40 is about 12 inches long, has a truncated shape, is somewhat wider than the primary blade 38 and has a maximum width of about 4¼ inches. Both blades 38, 40 are about 3/16 inches thick and have a flat top surface. An elongated, flat triangular fin or keel 50 is mounted on the bottom 52 of the primary blade 38 proximate the shaft 42 as best shown in FIG. 3. The flange or keel 50 runs parallel to the axis of the primary blade 38 and perpendicular to its flat bottom 52. The depending flange or keel 50 is widest at the shaft 42 where it has a width of about ⅜ inch. The length of the keel 50 is slightly less than one-half the length of the blade 38. The keel 50 has a thickness of about ¼ inch.

The secondary blade 40 carries an arch support form 56 which is pivotally mounted on the blade 40 by a removable pivot pin 58. The arch support form 56 is shaped generally like the arch of a human foot except that it is symmetrically shaped relative to the pivot pin 58 so that it can be used with both a right foot and left foot. If desired, several different size arch support forms (not shown) can be interchangeably used as required for different foot sizes.

The casting stand support frame comprising the base 12 and post 20 is preferably made of strong and lightweight square aluminum tubing. If desired, the turnstile 36 may include more than two blades to include additional limb support blades of different sizes and mounted at different angles of orientation to the turnstile axis. In the preferred embodiment illustrated in FIGS. 1-9, the height of the vertical post 20 is adjustable so that each blade 38, 40 can be positioned from 11 to 19 inches above the floor. That range is considered adequate for adult patients sitting on an examination table 32 inches above the floor.

The casting stand 10 is adapted to be folded for storage and transportation. Preferably, the upper center post section 24 is lowered fully and locked in place before folding the stand 10. The center post 20 is then pivoted into engagement with the base 12. The secondary blade 40 is preferably placed in the working position before the casting stand 10 is folded so that the narrower primary blade 38 is folded with the post 20 across the leg 16 of the base 12.

The preferred method of using the casting stand 10 is as follows The casting stand 10 is unfolded and erected. The turnstile 36 is positioned so that the primary blade 38 is in the upper, horizontal working position. The patient's foot is placed on the primary blade 38 with the patient's heel aligned with the outer rounded end 54 of the blade 38 to reduce or prevent internal space within the cast at the outer end of the blade 38. The height of the blade 38 is adjusted with the clamping screw 26 to properly position the patient's foot and ankle. In most cases, it is desirable to form an angle of approximately 90° between the tibia and plantar surface of the foot. A stockinette is applied around the foot. Cast padding is wrapped around the foot and primary blade 38, preferably to provide about 3-4 layers of cast padding at the malleoli and calcaneus areas of the foot and at the forefoot. Preferably, only 1-2 layers of cast padding are wrapped around the midcalf area. The depending keel 50 increases the circumference of the cast opening in the toe area.

While the patient's foot is supported by the primary blade 38, the casting material, which is preferably either fiberglass or plaster, is applied. When plaster is used, a basin is placed directly under the foot to catch any wet plaster and other debris dripping from the cast. The physician or technician, who is preferably sitting on a low stool, has full view of the medial/lateral position of the foot during application of the cast.

If required, a reinforcing splint (not shown) is applied to the plantar surface of the patient's foot, around the heel and up the calf. The splint is clamped to the top of the primary blade 38 with a suitable clamp (not shown) immediately in front of the patient's toes so that the assistance of another person is not required for that purpose. The splint is then covered with another layer of casting material molded smoothly about the first layer.

The plaster or other casting material is permitted to set sufficiently to hold the ankle before removal of the primary blade 38, but is sufficiently soft to be moldable to a final shape. The foot is then temporarily held by the physician or technician while the casting stand 10 is retracted from the patient to remove the primary blade 38 through the opening in the toe end of the cast. The secondary blade 40 is then rotated to the upper, horizontal working position and the arch support form 56 is positioned for alignment with the arch of the patient's foot. The casting stand 10 is then repositioned and the patient's foot is placed on the secondary blade 40 with the arch support form 56 under the arch of the patient's foot. The arch support 56 form causes the partially set cast to conform to the shape of the patient's arch, i.e., to form the cast around the malleoli, the proximal tibial area, the calcaneus, and the metatarsal heads, etc. to provide comfort and proper arch support. With the patient's foot resting on the secondary blade 40, the toe area of the cast is flattened out slightly by the support pressure of the blade 40 to permit extra space to develop so that the toes and metatarsals can spread within the extra space provided within the front end of the cast by the depending keel 50. Thus, the stand results in the formation of an arch support, and a generally flat surface elsewhere on the sole of the foot.

When a fiberglass cast is applied, a wet elastic bandage is applied over the cast to encourage compaction of the layers and to help the plaster set. A tub or basin is placed under the cast to catch any drippings.

The described casting stand 10 is particularly useful for application of short leg casts, including walking casts. Short leg casts are often used for the realignment of the ankle or distal tibia after a fracture or severe sprain has occurred. Short leg casts are also used for alignment and stabilization of the foot and ankle after tendon transfers, skin grafts and other soft tissue and ligament repairs. In the latter situation, the cast must be changed every few days to gradually improve the position of the ankle or foot against the contracted or scarred ligaments.

As will be apparent to persons skilled in the art, various modifications and adaptations of the structure described above will become readily apparent without departure from the spirit and scope of the invention, the scope of which is defined in the appended claims.

What is claimed is:

1. A casting stand, comprising a support base, an elongated upright post mounted on and supported by the base, and a turnstile-like limb support rotor including a rotor hub rotatably mounted on the post at an oblique angle to a horizontal plane, and a plurality of differently shaped elongated limb supports each having an inner end connected to the rotor hub, and each being specially configured to support a limb, the supports being adapted to be selectively and individually placed in respective working positions by rotation of the rotor hub, one of the limb supports including a thin blade for receiving and supporting a foot for applying a cast around the foot and blade.

2. A casting stand according to claim 1, further comprising means for holding the rotor in stationary positions corresponding to the working positions of the supports.

3. A casting stand according to claim 2, wherein the elongated limb supports extend outwardly at oblique angles relative to the longitudinal axis of the rotor hub.

4. A casting stand according to claim 1, wherein at least one of the elongated limb supports has a generally horizontal working position.

5. A casting stand according to claim 3 where the turnstile-like rotor has two of said elongated supports which in combination with the shaft have a generally Y-shaped configuration.

6. A casting stand according to claim 1, wherein the thin blade has a foot supporting surface with an inner toe end and an outer free heel end and an enlargement for enlarging the circumference of a cast applied around the foot and blade at the toe end of the supporting surface.

7. A casting stand according to claim 6, wherein the enlargement is formed by a keel depending from the blade.

8. A casting stand according to claim 1, wherein one of the elongated supports comprises a foot supporting surface and a separate arch form mounted on the supporting surface and shaped to form a cast to conform generally to the arch of a foot.

9. A casting stand according to claim 8, wherein the separate arch form can be selectively mounted on the supporting surface for a right foot and left foot.

10. A casting stand according to claim 1, wherein the upright post comprises a plurality of telescoping sections which are relatively adjustable for adjusting the height of the turnstile-like rotor.

11. A casting stand according to claim 5 wherein the upright post is pivotally mounted on the base for folding the post and turnstile-like rotor into engagement with the base for storage.

12. A casting stand according to claim 2, wherein the means for holding the rotor is a detent mechanism.

13. A casting stand comprising a support frame having a base for supporting the stand on the floor, and turnstile-like limb support means mounted on the frame above the base, the limb support means rotatably having first and second separate limb support blades, each having a support surface and being selectively and independently useable for supporting a foot, a keel depending from one of the support blades to enlarge a cast allied around the foot and blade at the toe area of the cast, and an arch support form adapted to be selectively mounted on the support surface of the other blade for selective use with a right foot and left foot.

14. A limb support mechanism for supporting a limb for applying a cast around the limb, comprising a support frame and a turnstile-like rotor including a rotor hub rotatably mounted on the support frame at an oblique angle to a horizontal plane, the turnstile-like rotor having a plurality of elongated limb supports each having an inner end which is connected to the rotor hub, the supports being adapted to be selectively and individually placed in respective working positions by rotation of the rotor hub on the support frame, one of the limb supports including a foot support surface having an arch support formed thereon and extending upward therefrom.

15. A limb support mechanism according to claim 14 wherein the turnstile-like rotor is rotatably mounted on the support frame for rotation about an axis inclined downwardly approximately 45° from the horizontal, and wherein the turnstile-like rotor has at least two elongated limb supports, each having a longitudinal axis in the plane of and axis of the turnstile and extending at an angle of approximately 45° to the axis longitudinal of the turnstile-like rotor.

16. A casting stand according to claim 14, further comprising means for holding the rotor in stationary positions corresponding to the working positions of the supports.

17. A casting stand according to claim 16, wherein the means for holding the rotor is a detent mechanism.

* * * * *

UNITED STATES PATENT AND TRADEMARK OFFICE
CERTIFICATE OF CORRECTION

PATENT NO. : 5,242,140
DATED : September 7, 1993
INVENTOR(S) : Gerald D. Ritland It is certified that error appears in the above-indentified patent and that said Letters Patent is hereby corrected as shown below:

Column 6, Claim 13, line 16, change "allied" to --applied--.

Column 6, Claim 15, line 41, insert --longitudinal-- before "axis" and delete "longitudinal" after "axis".

Signed and Sealed this

Thirtieth Day of August, 1994

Attest:

BRUCE LEHMAN

*Attesting Officer*   *Commissioner of Patents and Trademarks*